(12) United States Patent
Abdelghani

(10) Patent No.: US 10,065,907 B2
(45) Date of Patent: Sep. 4, 2018

(54) ISOPRENE EXTRACTION WITH PRESERVED C5 FEEDSTOCK

(71) Applicant: SABIC Global Technologies B.V., Bergen op Zoom (NL)

(72) Inventor: Mohamed Sabri Abdelghani, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/537,442

(22) PCT Filed: Dec. 15, 2015

(86) PCT No.: PCT/IB2015/059635
§ 371 (c)(1),
(2) Date: Jun. 19, 2017

(87) PCT Pub. No.: WO2016/097999
PCT Pub. Date: Jun. 23, 2016

(65) Prior Publication Data
US 2017/0362144 A1    Dec. 21, 2017

Related U.S. Application Data

(60) Provisional application No. 62/162,121, filed on May 15, 2015, provisional application No. 62/093,557, filed on Dec. 18, 2014.

(51) Int. Cl.
*C07C 7/08* (2006.01)
*C07C 7/10* (2006.01)
(Continued)

(52) U.S. Cl.
CPC ............... *C07C 7/005* (2013.01); *C07C 7/08* (2013.01); *C07C 7/10* (2013.01); *C07C 11/18* (2013.01);
(Continued)

(58) Field of Classification Search
None
See application file for complete search history.

(56) References Cited

U.S. PATENT DOCUMENTS 2,459,403 A * 1/1949 Ahrens ................... C07C 7/005
203/54
2,623,844 A * 12/1952 Scheeline ............... C07C 7/005
203/44
(Continued)

FOREIGN PATENT DOCUMENTS

CN    101423450 A    5/2009
CN    101723788 A    6/2010
(Continued)

OTHER PUBLICATIONS

Chinese Patent No. 101423450; Date of Publication: May 6, 2009; Abstract Only, 1 page.
(Continued)

*Primary Examiner* — Tam M Nguyen
(74) *Attorney, Agent, or Firm* — Cantor Colburn LLP

(57) ABSTRACT

A process for extracting isoprene from a pyrolysis gas mixture or a C5 fraction wherein isoprene is purified by plural extractive distillations in the presence of a polar solvent and cyclopentadiene is effectively removed and recycled as a feedstock without being converted into its dimer, dicyclopentadiene. The isoprene recovered from the process described is more than 99.5% pure.

19 Claims, 1 Drawing Sheet

(51) Int. Cl.
  *C07C 11/18* (2006.01)
  *C07C 13/15* (2006.01)
  *C10G 7/08* (2006.01)
  *C07C 7/00* (2006.01)
  *C07C 13/61* (2006.01)

(52) U.S. Cl.
  CPC .............. *C07C 13/15* (2013.01); *C07C 13/61* (2013.01); *C10G 7/08* (2013.01)

(56) References Cited

U.S. PATENT DOCUMENTS

| | | | |
|---|---|---|---|
| 3,230,157 A * | 1/1966 | Hill | C07C 7/005 |
| | | | 203/53 |
| 3,436,438 A | 4/1969 | Takao et al. | |
| 3,439,060 A | 4/1969 | Kempton | |
| 3,497,566 A | 2/1970 | Schleppinghoff et al. | |
| 3,510,405 A | 5/1970 | Takao et al. | |
| 3,775,259 A * | 11/1973 | Sarno | C07C 7/005 |
| | | | 203/54 |
| 3,947,506 A * | 3/1976 | Lybarger | C07C 7/005 |
| | | | 585/259 |
| 4,081,332 A | 3/1978 | Hein | |
| 4,471,153 A | 9/1984 | Throckmorton | |
| 4,647,344 A | 3/1987 | Lindner et al. | |

| | | | |
|---|---|---|---|
| 2011/0034747 A1 * | 2/2011 | Gartside | C07C 4/04 |
| | | | 585/326 |

FOREIGN PATENT DOCUMENTS

| | | | |
|---|---|---|---|
| GB | 1072687 A | | 6/1967 |
| GB | 1340149 A | | 12/1973 |
| GB | 1344219 | * | 1/1974 |
| GB | 1417733 A | | 12/1975 |

OTHER PUBLICATIONS

Chinese Patent No. 101723788; Date of Publication: Jun. 9, 2010; Abstract Only, 2 pages.
International Search Report for International Application No. PCT/IB2015/059635; International Filing Date: Dec. 15, 2015; dated Mar. 14, 2016; 5 Pages.
Liao et al., "Separation of cracking C5 fraction through extractive distillation with added salt N-methyl pyrrolidone", English Translation, 16 pages.
Wang, S. et al., "Analysis of C5 fraction and extractive distillation solvent by two-dimensional gas chromatography with heart-cutting technique", Anal. Methods, 2012, vol. 4, 3739-3743.
Written Opinion of the International Searching Authority for International Application No. PCT/IB2015/059635; International Filing Date: Dec. 15, 2015; dated Mar. 14, 2016; 9 Pages.

* cited by examiner

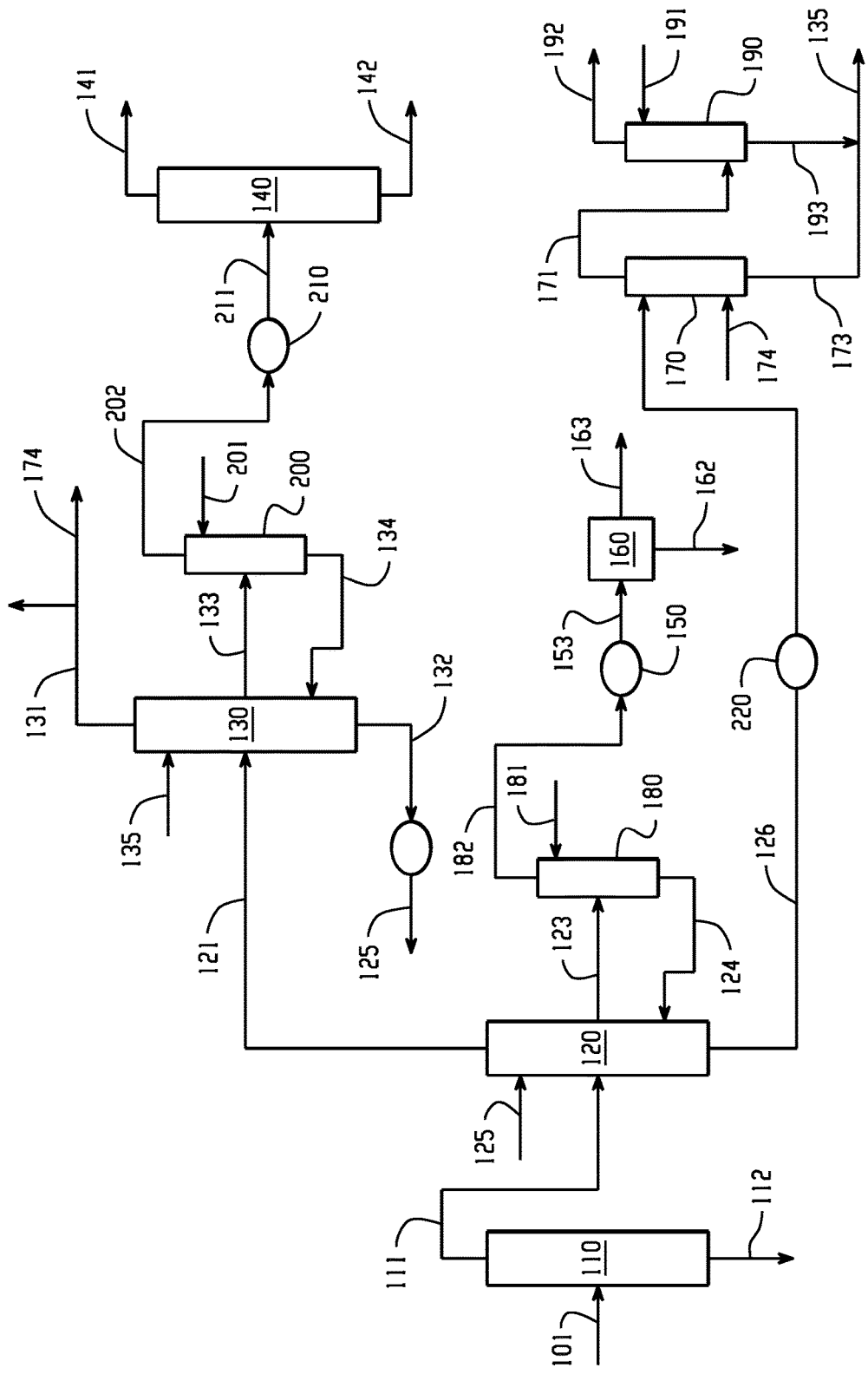

ISOPRENE EXTRACTION WITH PRESERVED C5 FEEDSTOCK

CROSS REFERENCE TO RELATED APPLICATIONS

This application is a 371 of International Application No. PCT/IB2015/059635, filed Dec. 15, 2015, which claims priority to U.S. Application No. 62/162,121, filed May 15, 2015, and U.S. Application No. 62/093,557 filed Dec. 18, 2014, all of which are incorporated herein by reference in their entirety.

TECHNICAL FIELD

Disclosed herein is a process for producing isoprene. More specifically, disclosed herein is a process for producing isoprene by extracting isoprene from pyrolysis gas or $C_5$ hydrocarbon mixtures wherein the $C_5$ hydrocarbons may be preserved as feedstocks for other petrochemical processes.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present application.

Isoprene, or 2-methyl-1,3-butadiene with the formula $CH_2=C(CH_3)CH=CH_2$, is an organic compound naturally produced by many plants. For example, it is a monomer of natural rubber. Under standard conditions, isoprene is a colorless liquid with an aromatic odor. Isoprene is insoluble in water, soluble in alcohol and because of its low boiling point and double bonds, is very reactive.

The polymerization of isoprene using catalysts yields synthetic rubber that closely resembles natural rubber and is used in a wide variety of rubber applications. Examples of synthetic rubber include polyisoprene as well as copolymers styrene-isoprene and butyl rubber. Polyisoprene is used in medical equipment, baby bottle teats/nipples, toys, shoe sole, tires, elastic films and threads for golf balls or textiles, adhesives, paints and coatings. Butyl rubber, made from isobutylene with a small amount of isoprene in the presence of an aluminum chloride initiator, has outstanding impermeability to gases and is used, for example, in inner tubes and tires. Styrene-isoprene rubber is used in pressure sensitive adhesives.

High-purity isoprene is used almost entirely (90-95%) as a monomer in the production of synthetic rubber. Considerably smaller amounts of isoprene are converted as an intermediate into specialty chemicals, including vitamins, pharmaceuticals, flavorings and perfumes, and epoxy hardeners.

Some of the major challenges facing the isoprene market include insufficient supply and increasing prices.

There are several different methods for industrial production of isopropene. The choice of one method over another depends on the availability of the raw materials or feedstock and the economics of the selected process. These processes for producing isoprene are usually developed and routinely used by companies having access to petroleum-based feedstocks. Feedstocks include, for example, tertiary amylenes (dehydrogenation thereof) by Shell, acetylene and acetone by Snamprogetti, isobutylene and formaldehyde by IFP Energies Nouvelles, propylene by Goodyear.

Additionally, isoprene can be recovered from a $C_5$ hydrocarbon mixture or $C_5$ fraction. U.S. Pat. No. 3,510,405 describes a process of purifying isoprene wherein isoprene-containing cyclopentadiene is subject to extractive distillation in the presence of N-alkylated lower fatty acid amide solvent under anhydrous conditions thereby to obtain isoprene as the distillate of the extractive distillation.

U.S. Pat. No. 3,775,259 discloses a process of recovering isoprene from a cyclopentadiene-containing $C_5$ fraction in a two-stage extractive distillation in the presence of a selective polar solvent. During the process, cyclopentadiene is dimerized into dicyclopentadiene at a temperature of 80° C. to 120° C. for easy separation (by distillation) from the solvent.

U.S. Pat. No. 4,647,344 provides a process for recovering isoprene, penta-1,3-diene and cyclopentadiene by liquid-liquid extraction or extractive distillation, wherein the process temperature and the energy consumption can both be kept low.

GB Pat. Nos. 1,072,687, 1,340,149 and 1,417,733 disclose single-, two- and three-stage extraction distillation processes to recover isoprene from $C_5$ hydrocarbon mixtures, respectively.

All aforementioned patents are each incorporated herein by reference in its entirety.

Isoprene must be obtained with a high degree of purity when it is to be used for producing stereospecific polymers because the impurities would be extremely detrimental towards polymerization. In view of the foregoing, new methods of producing isoprene and even new feedstocks for isoprene production are sought to cope with global demand

BRIEF SUMMARY

Disclosed, in various embodiments, are processes for the extracting isoprene from a mixture comprising $C_5$ hydrocarbons.

A process of extracting isoprene from a mixture comprising $C_5$ hydrocarbons, comprises: feeding the mixture comprising $C_5$ hydrocarbons into a first extractive distillation column and extractively distilling the mixture by contact with a first polar solvent to form a first overhead product comprising isoprene and a first slip stream comprising cyclopentadiene and substantially no dicyclopentadiene; feeding the first overhead product to a second extractive distillation column and extractively distilling the first overhead product by contact with a second polar solvent to form a second overhead product comprising unextracted $C_5$ hydrocarbons and a second slip stream comprising isoprene and other hydrocarbons; washing the second slip stream with water in a solvent wash column; cooling the second overhead product in a cooler; and distilling the second overhead product in a distillation column to form a third overhead product comprising high-purity isoprene, and a bottom product.

A process of extracting isoprene from a mixture comprising $C_5$ hydrocarbons, comprises: feeding the mixture comprising $C_5$ hydrocarbons into a first extractive distillation column and extractively distilling the mixture by contact with a first polar solvent to form a first overhead product comprising isoprene and a first slip stream comprising cyclopentadiene and substantially no dicyclopentadiene; feeding the first overhead product to a second extractive distillation column and extractively distilling the first overhead product by contact with a second polar solvent to form a second overhead product comprising unextracted $C_5$ hydrocarbons and a second slip stream comprising isoprene and other hydrocarbons; removing solvent impurity in the second slip stream in a solvent wash column; cooling the second overhead product; and distilling the second overhead product in a distillation column to form a third overhead product comprising high-purity isoprene, and a bottom product.

A process of extracting isoprene from a Pygas mixture comprising $C_5$ to $C_{10}$ hydrocarbons, comprises: distilling the Pygas mixture in a depentanizer distillation column to form a first overhead product comprising $C_5$ hydrocarbons and a first bottom product comprising $C_6$ to $C_{10}$ hydrocarbons; feeding the first overhead product into a first extractive distillation column and extractively distilling the first overhead product by contact with a first polar solvent to form a second overhead product comprising isoprene, and a first slip stream comprising cyclopentadiene and substantially no dicyclopentadiene; feeding the second overhead product to a second extractive distillation column and extractively distilling the second overhead product by contacting with a second polar solvent to form a third overhead product comprising unextracted $C_5$ hydrocarbons, and a second slip stream comprising isoprene and other hydrocarbons; distilling the second slip stream; washing the second slip stream in a solvent wash column; cooling the second overhead product; and feeding the second overhead product to a distillation column to form a fourth overhead product comprising high-purity isoprene, and a bottom product.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 is a schematic diagram illustrating the isoprene purification process according to an embodiment.

DETAILED DESCRIPTION

According to a first aspect, disclosed herein is a process of extracting isoprene from a mixture comprising $C_5$ hydrocarbons, comprising distilling the mixture comprising $C_5$ hydrocarbons in a first extractive distillation column and extractively distilling the mixture by contacting it with a first polar solvent to form a first overhead product comprising isoprene.

In one embodiment, the process provides a first slip stream comprising cyclopentadiene and substantially no dicyclopentadiene.

In another embodiment, the first overhead product is fed to a second extractive distillation column and is extractively distilled by contact with a second polar solvent to form a second overhead product comprising unextracted $C_5$ hydrocarbons and a second slip stream comprising isoprene and other hydrocarbons.

In another embodiment, the process further includes distilling the second slip stream in a distillation column to form a third overhead product comprising high-purity isoprene and a bottom product.

In one embodiment, the process may further comprise cooling the first slip stream and separating the first slip stream into an oil fraction comprising cyclopentadiene and substantially no dicyclopentadiene and a water fraction comprising the first polar solvent.

In one embodiment, the process further includes recycling the oil fraction comprising cyclopentadiene and substantially no dicyclopentadiene to a cracker to form one or more olefins.

In one embodiment, the third overhead product has an isoprene purity of at least 99.5%.

In one embodiment, the polar solvent is N-2-methylpyrrolidone.

According to a second aspect, disclosed herein is a process of extracting isoprene from a Pygas mixture comprising $C_5$ to $C_{10}$ hydrocarbons, comprising distilling the Pygas mixture in a depentanizer distillation column to form a first overhead product comprising $C_5$ hydrocarbons and a first bottom product comprising $C_6$ to $C_{10}$ hydrocarbons.

In one embodiment, the first overhead product is fed to a first extractive distillation column and is extractively distilled by contacting it with a first polar solvent to form a second overhead product comprising isoprene.

In another embodiment, the process provides a first slip stream comprising cyclopentadiene and substantially no dicyclopentadiene.

In another embodiment, the second overhead product is fed to a second extractive distillation column and is extractively distilled by contact with a second polar solvent to form a third overhead product comprising unextracted $C_5$ hydrocarbons.

In one embodiment, the process provides a second slip stream comprising isoprene and other hydrocarbons.

In one embodiment, the second slip stream is distilled in a distillation column to form a fourth overhead product comprising high-purity isoprene and a bottom product.

In one embodiment, the process may further comprise cooling the first slip stream and separating the first slip stream into an oil fraction comprising cyclopentadiene and substantially no dicyclopentadiene and a water fraction comprising the first polar solvent.

In one embodiment, the process further includes recycling the oil fraction comprising cyclopentadiene and substantially no dicyclopentadiene to a cracker to form one or more olefins.

In one embodiment, the third overhead product has an isoprene purity of at least 99.5%.

In one embodiment, the polar solvent is N-2-methylpyrrolidone.

According to the present application, provided is a process of recovering isoprene in high purity from a Pygas gas stream by at least one extractive distillation with a polar solvent and optionally with a combination of other distillation methods. The process optionally does not include reactions such as catalytic hydrogenation and dimerization of cyclopentadiene to dicyclopentadiene. As cyclopentadiene is not converted into its dimer, it can be recycled to a cracker as feedstock.

Ethylene production through pyrolysis (steam cracking) produces several by-products, including a heavy $C_5$+ stream. The $C_5$+ cut is referred to in the oil and gas industry as pyrolysis gasoline or Pygas. Therefore, Pygas is a mixture of hydrocarbon compounds in $C_5$-$C_{10}$ boiling range (naptha range). The main constituent of Pygas is benzene (25%-50%) and other high-value components that may be separated and purified by distillation include isoprene, toluene and xylene. In one embodiment, the Pygas stream used as the starting feedstock for the isoprene recovery process of the present disclosure includes, for example, $C_5$-$C_{12}$ alkanes, $C_5$-$C_{10}$ cycloalkanes (napthenes), $C_5$-$C_{10}$ alkenes, $C_5$-$C_{10}$ cycloalkenes, $C_5$-$C_{10}$ alkynes, $C_8$-$C_{10}$ cycloalkynes, $C_5$-$C_{10}$ diolefins and cyclodienes. In one embodiment, the Pygas stream may contain traces of various hydrocarbons of less than 5 carbon atoms and/or hydrocarbons of more than 10 carbon atoms (e.g. up to 12 carbon atoms). These trace amounts are generally no more than 0.005% by mass, for example 0.002% to 0.003%, for example, 0.001% to 0.002%, for example, 0.0001%.

The isoprene product recovered at the end of any embodiment of the processes described herein can include at least 99.5% isoprene by mass, for example, 99.6% to 99.7%, for example, 99.8% to 99.9%. Therefore, "high-purity isoprene" as described herein refers to isoprene that is at least 99.5% pure (by mass), for example, 99.6% to 99.7% pure, for example, 99.8% to 99.9% pure. High-purity isoprene has a cyclopentadiene content lower than 0.5% by mass, for example, 0.3% to 0.4%, for example, 0.1% to 0.2%. In an embodiment, high-purity isoprene contains less than 5 parts per million (ppm) cyclopentadiene, for example, 1 to 3 ppm, for example, less than or equal to 1 ppm.

Distillation is a process of separating the component substance from a liquid mixture by selective vaporization and condensation. As used herein, extractive distillation is a type of distillation wherein the process takes places in the presence of a miscible, high-boiling, relatively non-volatile polar solvent. The solvent preferably forms no azeotrope with any of the other components in the mixture. Extractive distillation can effectively separate mixtures which are not easily separable by conventional fractional distillation, for example if the components to be separated form an azeotrope or if the differences in the relative volatilities are slight or near unity. In extractive distillation, the low-volatility, polar solvent is introduced to the distillation column in such amounts that the differences in the relative volatilities of the components to be separated become substantial enough for separation by distillation. Examples of solvents that may be used in extractive distillation include carboxamides such as dimethylformamide, diethylformamide, dimethylacetamide and N-formylmorpholine, acetonitrile, morpholine, furfural, N-2-methylpyrrolidone, butylrolacetone, ethylene glycol monomethyl ether, diethylene glycol monomethyl ether, 3-methoxypropionitrile, gamma-3-butyrolactone, and acetone and their mixtures with water. (C. S. Robinson et al., "Elements of Fractional Distillation", $4^{th}$ ed. McGraw-Hill Company, Inc., New York. 1959; U.S. Pat. Nos. 4,081,332 and 4,647,344-incorporated herein by reference in its entirety).

The polar solvent used in extractive distillation procedures described herein can be N-2-methylpyrrolidone (NMP), which has a boiling point of 202° C. to 204° C. The solvent can have a water content of up to 9.0% of the total weight of the diluted solvent, for example, 7.0 to 9.0%, for example, 7.5% to 8.5%. In one embodiment, the water content of NMP can be 8.3%. After the solvent has been mixed with the feedstock stream, the solvent can be present in the extractive distillation column tower at a concentration of 70 weight percent (wt. %) to 99 wt. %, for example, 85 wt. % to 98 wt. %, for example, 92 wt. % to 97.5 wt. %, based on the total mass of the solvent and the feedstock stream.

In one embodiment, the polar solvent consists of NMP and water.

In another embodiment, the polar solvent consists essentially of NMP and water and excludes components which may materially affect the volatility or solvency properties of the solvent mixture.

During fractional distillation, on the other hand, a mixture can be separated into its component parts or fractions according to their respective boiling points by heating them to a temperature at which one or more fractions of the compound will vaporize. Generally, the components or fractions boil at temperatures that differ by less than 25° C. from each other under a pressure of 1 atmosphere (atm). If the difference in boiling points is greater than 25° C., simple distillation is used. According to the present application, all non-extractive distillation columns, for example a depentanizer column, can operate by fractional distillation or simple distillation.

In general, to separate its components, a pyrolysis gasoline or Pygas stream is distilled in distillation columns or towers. The components can be collected as fractions, or as an overhead distillate stream, a slip stream, a side stream or a bottom stream.

Referring now to the drawings, wherein like reference numerals designate identical or corresponding parts throughout the several views.

In an exemplary embodiment of a novel isoprene purification process 100 as shown in FIG. 1, starting Pygas stream as previously described is first distilled in a depentanizer distillation column 110 via line 101. The depentanizer distillation column separates $C_5$ stream overhead 111 and $C_6$+ stream 112 as a bottom product. The $C_5$ stream 111 is then subject to a first extractive distillation in first extractive distillation column 120 wherein the $C_5$ stream is fed to the middle of first extractive column 120 via line 111. A polar solvent 125 such as NMP is fed to the top of first extractive distillation column 120. In first extractive distillation column 120, isoprene along with $C_5$ alkanes and $C_5$ alkenes are separated overhead. The overhead product mixture 121 contains isoprene, $C_5$ alkanes, $C_5$ alkenes and substantially no cyclopentadiene and no dicyclopentadiene (i.e. combined cyclopentadiene and dicyclopentadiene of less than 0.0001% of the total mass of the overhead product mixture). This overhead product mixture 121 proceeds to second extractive distillation column 130 via line 121. In a similar fashion as with first extractive distillation column 120, a polar solvent 135 such as NMP is fed to the top of second extractive distillation column 130. In second extractive distillation column 130, a $C_5$ mixture containing pentane, isopentane and 1-pentene leaves the column as an overhead distillate via line 131. The polar solvent 135 leaves second extractive distillation column 130 as a bottom product via line 132. Isoprene together with some remaining impurities such as 1,2-pentadiene and transpentadiene, cyclopentene and 2-methylpentene are withdrawn in the gas phase from the lower part of second extractive distillation column 130 through a slip stream 133. The slip stream 133 is fed to a solvent wash column 200 where the solvent is washed by a water stream 201 and exits a bottom of the solvent wash column 200 and is directed back to the second extractive distillation column 130. An overhead stream 202 is fed to cooler 210 and cooled stream 211 is directed to finishing distillation column 140 where isoprene is separated from remaining impurities. The isoprene recovered from line 141 is at least 99.5% pure (by mass), for example, 99.6% to 99.7% pure, for example, 99.8% to 99.9% pure. The remaining impurities exit finishing distillation column 140 as a bottom product via line 142.

As used herein, residence time is the duration between the exit of first overhead product 121 from first extractive column 120 and the exit of isoprene-containing slip stream 133 from second extractive column 130. In one embodiment, the residence time is preferably no longer than 12 hours, for example, less than 6 hours, for example, less than 3 hours, for example, less than 1 hour, for example, less than 30 minutes. Residence time for cyclopentadiene in the first extractive column 120 between the entry of feed 111 and removal in vapor draw stream 123 (e.g., slip stream 123) is less than or equal to 10 minutes, for example, less than or equal to 5 minutes, for example, less than or equal to 3 minutes.

In another embodiment, the isoprene extraction process uses $C_5$ hydrocarbon mixtures or $C_5$ fractions as the starting feedstock and therefore requires a distillation step with a depentanizer column to separate the isoprene from the remainder of pygas C6+ hydrocarbons. Such $C_5$ fractions are, like Pygas, obtained as a hydrocarbon fraction in, for example, the preparation of ethylene and/or propylene by thermal cleavage of a petroleum fraction, e.g. liquefied petroleum gas (LPG), naphtha, gas oil or the like, in the presence of steam. Such $C_5$ fractions may also be obtained in the catalytic dehydrogenation of pentanes and/or pentenes. $C_5$ fractions contain various types of $C_5$ hydrocarbons of different degrees of saturation, and furthermore contain small amounts (less than 0.005%) of hydrocarbons of less than 5 atoms and/or hydrocarbons of more than 5 atoms. Examples of $C_5$ hydrocarbons contained in $C_5$ fractions include, but are not limited to, n-pentane, isopentane, pent-1-ene, 2-methylbut-1-ene, 3-methylbut-1-ene, 2-methylbut-2-ene, transpent-2-ene, cis-pent-2-ene, isoprene, trans-penta-1,3-diene, cis-penta-1,3-diene, penta-1,4,-diene, penta-1-yne, pent-2-yne, isopropenylacetylene, isopropylacetylene, cyclopentane, cyclopentene and cyclopentadiene. $C_5$ fractions according to the present invention preferably contain no conjugated diolefins other than isoprene, or they may be present in trace amounts. These trace amounts are generally no more than 0.005% by mass, for example 0.002% to 0.003%, for example, 0.001% to 0.002%.

Cyclopentadiene is the main contaminant in isoprene extraction or recovery processes from $C_5$ fractions. Cyclopentadiene contamination in extracted isoprene is undesirable because it poisons the catalyst during the polymerization of isoprene. Since isoprene and cyclopentadiene have very similar boiling points (i.e. 34° C. and 39-43° C., respectively), it is very difficult to separate these two components by distillation methods such as fractional distillation and simple distillation. Therefore, extractive distillation is generally used to separate isoprene and cyclopentadiene.

Referring back to FIG. 1, the process can include features wherein cyclopentadiene is effectively removed as a vapor draw stream 123 from first extractive distillation column 120. Cyclopentadiene retains its value as a light material in the process disclosed herein because it is not reduced and dimerized into heavy dicyclopentadiene at elevated temperatures (e.g. 80 to 120° C.) as typically practiced in the art. The vapor draw stream 123 containing cyclopentadiene and other hydrocarbons from first extractive distillation column 120 is fed to a solvent washer column 180 where any traces of solvent can be washed with a water stream 181 and returned to first extractive distillation column 120 via stream 124. Overhead stream 182 is fed to cooler 150 to be quenched to a low temperature of 40° C. to 50° C., or 45° C. in one example. The cooled slip stream is then fed, via line 153, to an oil/water separator 160 where oil, cyclopentadiene and other hydrocarbons are separated from the water phase. The separated cyclopentadiene leaves oil/water separator 160 via line 163 to be mixed with the $C_6$+ hydrocarbons of the bottom stream of depentanizer distillation column 110. In this way, cyclopentadiene can then be hydrogenated to cyclopentane in a reactor that can be installed downstream and therefore can be recycled back to a cracker as feedstock, for example, for olefin production. If cyclopentadiene has been dimerized into dicyclopentadiene, the latter cannot be recycled as feedstock since it is heavy and is instead used as fuel. In other words, at the end of the isoprene extraction process as disclosed herein, the $C_5$ feedstock comprising cyclopentadiene has been preserved and can be recycled for other petrochemical processes.

The dimerization of cyclopentadiene into dicyclopentadiene proceeds slowly with residence times of up to 12 hours in a dimerization zone that takes up a large capacity. Therefore, the isoprene extraction process provided herein including all embodiments, is both cost effective and time efficient.

The water phase 162 separated from oil/water separator 160 is sent to a waste water system. An NMP stream 126 (e.g., a bottom solvent stream) leaving the first extractive column 120 will have traces of dimerized cyclopentadience as dicyclopentadience (DCPD) that has formed in the first extractive column 120. The NMP stream 126 is fed to cooler 220. The DCPD traces are removed from the NMP stream 126 in a liquid-liquid extraction column 170. In liquid-liquid extraction column 170, NMP is contacted with a slip stream 174 of unextracted product stream 131. A bottom product stream 173 (e.g., bottom solvent product stream) from liquid-liquid extraction column 170 contains purified NMP, while top product stream 171 contains DCPD dissolved in a $C_5$ stream and NMP. Top product stream 171 can then be sent to another liquid-liquid extraction column 190, where it is washed with water fed into the liquid-liquid extraction column 190 from water stream 191. Bottom product stream 193 contain an NMP water mixture that is directed to the second extractive column 130, while top product stream 192 contains $C_5$ and DCPD hydrocarbons free from NMP that is combined with the depentanizer bottom stream of $C_6$+ hydrocarbons 112.

The process disclosed herein includes at least the following embodiments:

Embodiment 1: A process of extracting isoprene from a mixture comprising $C_5$ hydrocarbons, comprising: feeding the mixture comprising $C_5$ hydrocarbons into a first extractive distillation column and extractively distilling the mixture by contact with a first polar solvent to form a first overhead product comprising isoprene and a first slip stream comprising cyclopentadiene and substantially no dicyclopentadiene; feeding the first overhead product to a second extractive distillation column and extractively distilling the first overhead product by contact with a second polar solvent to form a second overhead product comprising unextracted $C_5$ hydrocarbons and a second slip stream comprising isoprene and other hydrocarbons; washing the second slip stream with water in a solvent wash column; cooling the second overhead product in a cooler; and distilling the second overhead product in a distillation column to form a third overhead product comprising high-purity isoprene, and a bottom product.

Embodiment 2: A process of extracting isoprene from a mixture comprising $C_5$ hydrocarbons, comprising: feeding the mixture comprising $C_5$ hydrocarbons into a first extractive distillation column and extractively distilling the mixture by contact with a first polar solvent to form a first overhead product comprising isoprene and a first slip stream comprising cyclopentadiene and substantially no dicyclopentadiene; feeding the first overhead product to a second extractive distillation column and extractively distilling the first overhead product by contact with a second polar solvent to form a second overhead product comprising unextracted $C_5$ hydrocarbons and a second slip stream comprising isoprene and other hydrocarbons; removing solvent impurity in the second slip stream in a solvent wash column; cooling the second overhead product; and distilling the second overhead product in a distillation column to form a third overhead product comprising high-purity isoprene, and a bottom product.

Embodiment 3: The process of Embodiment 1 or Embodiment 2, further comprising washing the first slip stream with water in a solvent wash column and cooling the first overhead product and separating the first slip stream into an oil fraction comprising cyclopentadiene and substantially no dicyclopentadiene and a water fraction comprising the polar solvent.

Embodiment 4: The process of any of Embodiments 1-3, further comprising treating a bottom solvent stream of the first extractive distillation column to remove dicyclopentadiene impurity by contacting the bottom solvent stream in a liquid-liquid extraction column, obtaining a purified bottom solvent product stream and a top product stream comprising hydrocarbons and dicyclopentadiene.

Embodiment 5: The process of Embodiment 4, further comprising washing the top product stream with water in a second liquid-liquid extraction column to remove solvent from the hydrocarbons and returning the solvent as a co-feed to the second extractive distillation column and sending the hydrocarbons to a cracker as a feed material.

Embodiment 6: The process of any of Embodiments 1-5, further comprising recycling the oil fraction comprising cyclopentadiene to a cracker to form one or more olefins.

Embodiment 7: The process of any of Embodiments 1-6, wherein the third overhead product has an isoprene purity of at least 99.5% by mass.

Embodiment 8: The process of any of Embodiments 1-7, wherein the first polar solvent and the second polar solvent are N-2-methylpyrrolidone.

Embodiment 9: A process of extracting isoprene from a Pygas mixture comprising $C_5$ to $C_{10}$ hydrocarbons, comprising: distilling the Pygas mixture in a depentanizer distillation column to form a first overhead product comprising $C_5$ hydrocarbons and a first bottom product comprising $C_6$ to $C_{10}$ hydrocarbons; feeding the first overhead product into a first extractive distillation column and extractively distilling the first overhead product by contact with a first polar solvent to form a second overhead product comprising isoprene, and a first slip stream comprising cyclopentadiene and substantially no dicyclopentadiene; feeding the second overhead product to a second extractive distillation column and extractively distilling the second overhead product by contacting with a second polar solvent to form a third overhead product comprising unextracted $C_5$ hydrocarbons, and a second slip stream comprising isoprene and other hydrocarbons; distilling the second slip stream; washing the second slip stream in a solvent wash column; cooling the second overhead product; and feeding the second overhead product to a distillation column to form a fourth overhead product comprising high-purity isoprene, and a bottom product.

Embodiment 10: The process of Embodiment 9, further comprising cooling the first washed slip stream and separating the first washed slip stream into an oil fraction comprising cyclopentadiene and substantially no dicyclopentadiene and a water fraction comprising the polar solvent.

Embodiment 11: The process of Embodiment 10, further comprising recycling the oil fraction comprising cyclopentadiene to a cracker to form one or more olefins.

Embodiment 12: The process of any of Embodiments 9-11, wherein the fourth overhead product has an isoprene purity of at least 99.5% by mass.

Embodiment 13: The process of any of Embodiments 9-12, wherein the first polar solvent and the second polar solvent are N-2-methylpyrrolidone In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

I claim:

1. A process of extracting isoprene from a mixture comprising $C_5$ hydrocarbons, comprising:
    feeding the mixture comprising $C_5$ hydrocarbons into a first extractive distillation column and extractively distilling the mixture by contact with a first polar solvent to form a first overhead product comprising isoprene and a first slip stream comprising cyclopentadiene and substantially no dicyclopentadiene;
    feeding the first overhead product to a second extractive distillation column and extractively distilling the first overhead product by contact with a second polar solvent to form a second overhead product comprising unextracted $C_5$ hydrocarbons and a second slip stream comprising isoprene and other hydrocarbons;
    washing the second slip stream with water in a solvent wash column;
    cooling the second overhead product in a cooler; and
    distilling the second slip stream in a distillation column to form a third overhead product comprising high-purity isoprene, and a bottom product.

2. A process of extracting isoprene from a mixture comprising $C_5$ hydrocarbons, comprising:
    feeding the mixture comprising $C_5$ hydrocarbons into a first extractive distillation column and extractively distilling the mixture by contact with a first polar solvent to form a first overhead product comprising isoprene and a first slip stream comprising cyclopentadiene and substantially no dicyclopentadiene;
    feeding the first overhead product to a second extractive distillation column and extractively distilling the first overhead product by contact with a second polar solvent to form a second overhead product comprising unextracted $C_5$ hydrocarbons and a second slip stream comprising isoprene and other hydrocarbons;
    removing solvent impurity in the second slip stream in a solvent wash column;
    cooling the second slip stream; and
    distilling the second slip stream in a distillation column to form a third overhead product comprising high-purity isoprene, and a bottom product.

3. The process of claim 1, further comprising washing the first slip stream with water in a solvent wash column and cooling the first overhead product and separating the first slip stream into an oil fraction comprising cyclopentadiene and substantially no dicyclopentadiene and a water fraction comprising the polar solvent.

4. The process of claim 1, further comprising treating a bottom solvent stream of the first extractive distillation column to remove dicyclopentadiene impurity by contacting the bottom solvent stream in a liquid-liquid extraction column, obtaining a purified bottom solvent product stream and a top product stream comprising hydrocarbons and dicyclopentadiene.

5. The process of claim 4, further comprising washing the top product stream with water in a second liquid-liquid extraction column to remove solvent from the hydrocarbons and returning the solvent as a co-feed to the second extractive distillation column and sending the hydrocarbons to a cracker as a feed material.

6. The process of claim 1, further comprising recycling the oil fraction comprising cyclopentadiene to a cracker to form one or more olefins.

7. The process of claim 1, wherein the third overhead product has an isoprene purity of at least 99.5% by mass.

8. The process of claim 1, wherein the first polar solvent and the second polar solvent are N-2-methylpyrrolidone.

9. A process of extracting isoprene from a Pygas mixture comprising $C_5$ to $C_{10}$ hydrocarbons, comprising:
    distilling the Pygas mixture in a depentanizer distillation column to form a first overhead product comprising $C_5$ hydrocarbons and a first bottom product comprising $C_6$ to $C_{10}$ hydrocarbons;
    feeding the first overhead product into a first extractive distillation column and extractively distilling the first overhead product by contact with a first polar solvent to form a second overhead product comprising isoprene, and a first slip stream comprising cyclopentadiene and substantially no dicyclopentadiene;
    feeding the second overhead product to a second extractive distillation column and extractively distilling the second overhead product by contacting with a second polar solvent to form a third overhead product comprising unextracted $C_5$ hydrocarbons, and a second slip stream comprising isoprene and other hydrocarbons;
    distilling the second slip stream;
    washing the second slip stream in a solvent wash column;
    cooling the second slip stream; and
    feeding the second slip stream to a distillation column to form a fourth overhead product comprising high-purity isoprene, and a bottom product.

10. The process of claim 9, further comprising cooling the first washed slip stream and separating the first washed slip stream into an oil fraction comprising cyclopentadiene and substantially no dicyclopentadiene and a water fraction comprising the polar solvent.

11. The process of claim 10, further comprising recycling the oil fraction comprising cyclopentadiene to a cracker to form one or more olefins.

12. The process of claim 9, wherein the fourth overhead product has an isoprene purity of at least 99.5% by mass.

13. The process of claim 1, wherein the first polar solvent and the second polar solvent are N-2-methylpyrrolidone.

14. The process of claim 2, further comprising washing the first slip stream with water in a solvent wash column and cooling the first overhead product and separating the first slip stream into an oil fraction comprising cyclopentadiene and substantially no dicyclopentadiene and a water fraction comprising the polar solvent.

15. The process of claim 2, further comprising treating a bottom solvent stream of the first extractive distillation column to remove dicyclopentadiene impurity by contacting the bottom solvent stream in a liquid-liquid extraction column, obtaining a purified bottom solvent product stream and a top product stream comprising hydrocarbons and dicyclopentadiene.

16. The process of claim 15, further comprising washing the top product stream with water in a second liquid-liquid extraction column to remove solvent from the hydrocarbons and returning the solvent as a co-feed to the second extractive distillation column and sending the hydrocarbons to a cracker as a feed material.

17. The process of claim 2, further comprising recycling the oil fraction comprising cyclopentadiene to a cracker to form one or more olefins.

18. The process of claim 2, wherein the third overhead product has an isoprene purity of at least 99.5% by mass.

19. The process of claim 2, wherein the first polar solvent and the second polar solvent are N-2-methylpyrrolidone.

* * * * *